(12) United States Patent
Lin et al.

(10) Patent No.: US 10,413,322 B2
(45) Date of Patent: Sep. 17, 2019

(54) ASSEMBLING SURGICAL ACCESS DEVICE

(71) Applicant: INTAI TECHNOLOGY CORP., Taichung (TW)

(72) Inventors: Dian-Ying Lin, Taichung (TW); Yi-Jen Jiang, Taipei (TW); Shih-Chang Chuang, Taichung (TW); Yung-Fang Tsai, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 217 days.

(21) Appl. No.: 15/255,146

(22) Filed: Sep. 2, 2016

(65) Prior Publication Data

US 2017/0112529 A1    Apr. 27, 2017

Related U.S. Application Data

(60) Provisional application No. 62/246,621, filed on Oct. 27, 2015.

(51) Int. Cl.
    *A61B 1/32*    (2006.01)
    *A61B 17/34*   (2006.01)
    *A61B 17/00*   (2006.01)

(52) U.S. Cl.
    CPC ...... *A61B 17/3421* (2013.01); *A61B 17/3417* (2013.01); *A61B 2017/0042* (2013.01); *A61B 2017/347* (2013.01); *A61B 2017/3445* (2013.01); *A61B 2017/3466* (2013.01); *A61B 2217/005* (2013.01); *A61B 2217/007* (2013.01)

(58) Field of Classification Search
    CPC ............ A61B 17/3423; A61B 17/3421; A61B 17/0218; A61B 17/3417; A61B 2090/103; A61B 2017/0042; A61B 2017/00477; A61B 2017/0225; A61B 2017/3445; A61B 2017/3466; A61B 2017/347
    USPC ....... 600/201, 208, 213, 226, 227–229, 234, 600/204–206
    See application file for complete search history.

(56) References Cited

U.S. PATENT DOCUMENTS

| | | | |
|---|---|---|---|
| 8,323,185 B2 | 12/2012 | Perez-Cruet et al. | |
| 2005/0209510 A1* | 9/2005 | Bonadio | A61B 90/35 600/208 |
| 2005/0277811 A1* | 12/2005 | Richards | A61B 1/303 600/184 |

(Continued)

FOREIGN PATENT DOCUMENTS

| | | |
|---|---|---|
| CN | 101711694 B | 7/2014 |
| CN | 102210598 B | 6/2015 |
| EP | 2138118 B1 | 1/2013 |

*Primary Examiner* — Kevin T Truong
*Assistant Examiner* — Jessica Weiss
(74) *Attorney, Agent, or Firm* — CKC & Partners Co., LLC

(57) ABSTRACT

An assembling surgical access device includes a flexible tube and a connecting structure. The flexible tube includes a tube body and a positioning portion connected to the tube body. The connecting structure is connected to the flexible tube, and includes a housing and a tube fixing member. The housing includes a side wall, an end wall, a fixing portion and a tube hole. The fixing portion is connected to the positioning portion of the flexible tube, and the tube body is disposed through the tube hole. The tube fixing member is engaged into the side wall so as to position the positioning portion between the end wall and the tube fixing member.

17 Claims, 15 Drawing Sheets

(56) References Cited

U.S. PATENT DOCUMENTS

| | | | |
|---|---|---|---|
| 2006/0247500 A1* | 11/2006 | Voegele | A61B 1/32 600/208 |
| 2010/0022958 A1 | 1/2010 | Moreno, Jr. et al. | |
| 2010/0081880 A1* | 4/2010 | Widenhouse | A61B 17/3462 600/201 |
| 2010/0280326 A1 | 11/2010 | Hess et al. | |
| 2011/0028793 A1* | 2/2011 | Martin | A61B 17/0293 600/208 |
| 2011/0028794 A1 | 2/2011 | Widenhouse et al. | |
| 2011/0046449 A1 | 2/2011 | Minnelli et al. | |
| 2011/0245619 A1 | 10/2011 | Holcomb | |
| 2012/0197087 A1* | 8/2012 | Smith | H04L 41/026 600/208 |
| 2013/0190573 A1* | 7/2013 | Smith | A61B 17/0218 600/207 |
| 2014/0121466 A1 | 5/2014 | Okoniewski et al. | |
| 2015/0065808 A1* | 3/2015 | Van Wyk | A61B 17/3462 600/208 |

* cited by examiner

ASSEMBLING SURGICAL ACCESS DEVICE

RELATED APPLICATIONS

This application claims priority to U.S. Provisional Application Ser. No. 62/246,621, filed Oct. 27, 2015, which is herein incorporated by reference.

BACKGROUND

Technical Field

The present disclosure relates to a surgical access device. More particularly, the present disclosure relates to an assembling surgical access device.

Description of Related Art

Minimally invasive surgical procedures, such as arthroscopic, endoscopic and laparoscopic procedures, permit surgery to be performed on organs, tissues and vessels far removed from an opening within the tissue. Arthroscopic, endoscopic or laparoscopic procedure generally requires that any surgical instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the surgical instrument to preserve the integrity and tightness.

Minimally invasive procedures have several advantages over traditional open surgery, including less patient trauma, reduced recovery time reduced potential for infection, etc. However, despite its recent success and overall acceptance as a preferred surgical technique, minimally invasive surgery, such as arthroscopy, has several disadvantages. In particular, the position of the arthroscopic instruments and arthroscopy has proven to be difficult in surgical procedures. In addition, when the user operates the arthroscopy and the surgical instrument with conventional assembling surgical access devices, the user only watch the display in the fixed position and it is not adaptable to the various requirements in surgical procedures. Moreover, many conventional assembling surgical access devices are complex, involving multiple components and accompanying assembly requirements. Therefore, an assembling surgical access device having simple structure and convenient operation is commercially desirable.

SUMMARY

According to one aspect of the present disclosure, an assembling surgical access device includes a flexible tube and a connecting structure. The flexible tube includes a tube body and a positioning portion connected to the tube body. The connecting structure is connected to the flexible tube and includes a housing and a tube fixing member. The housing includes a side wall, an end wall, a fixing portion and a tube hole. The fixing portion is connected to the positioning portion of the flexible tube, and the tube body is disposed through the tube hole. The tube fixing member is engaged into the side wall so as to position the positioning portion between the end wall and the tube fixing member.

According to another aspect of the present disclosure, an assembling surgical access device includes a flexible tube, a connecting structure and a cover. The flexible tube includes a tube body and a positioning portion connected to the tube body. The connecting structure is connected to the flexible tube and includes a housing and a tube. The housing includes a side wall, an end wall, a fixing portion, a tube hole, an inlaid hole and an upper slot. The fixing portion is connected to the positioning portion of the flexible tube. The tube body is disposed through the tube hole, and the tube hole is corresponding to the inlaid hole. The tube fixing member is engaged into the side wall so as to position the positioning portion between the end wall and the tube fixing member. The cover has a nose portion and a lid portion. The nose portion is connected to the lid portion, and the nose portion is engaged by the upper slot.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1A:
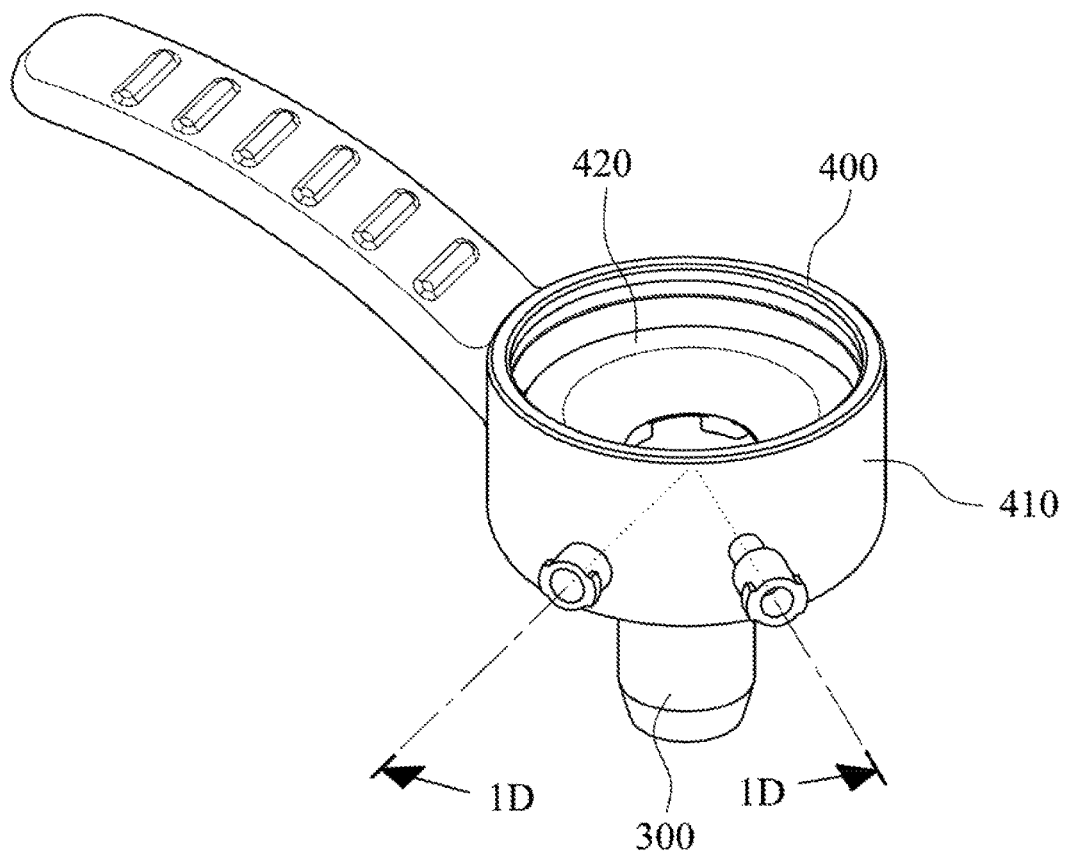
FIG. 1A shows a schematic view of an assembling surgical access device according to one embodiment of the present disclosure.
Figure 1B:
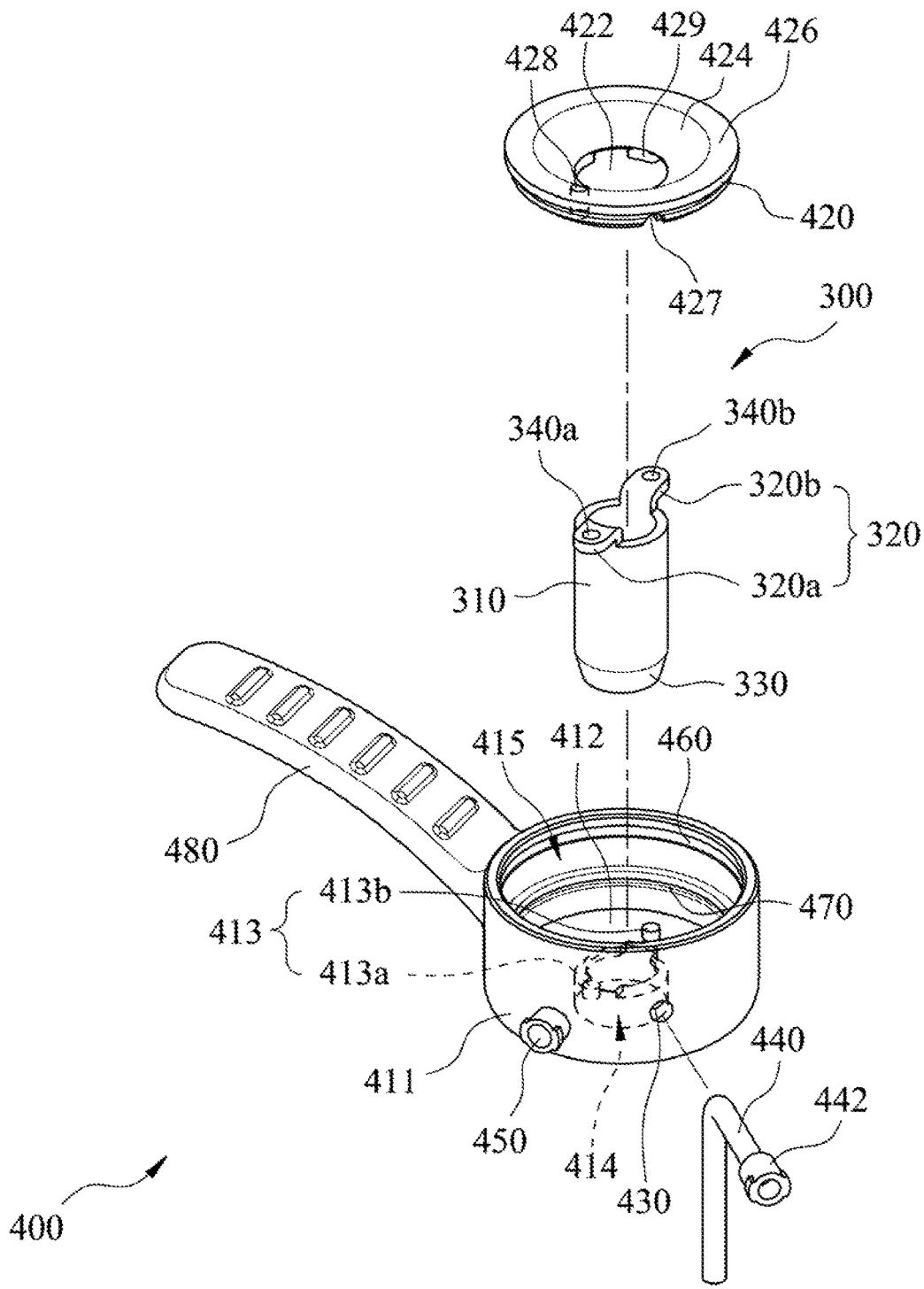
FIG. 1B shows one exploded view of the assembling surgical access device of FIG. 1A.
Figure 1C:
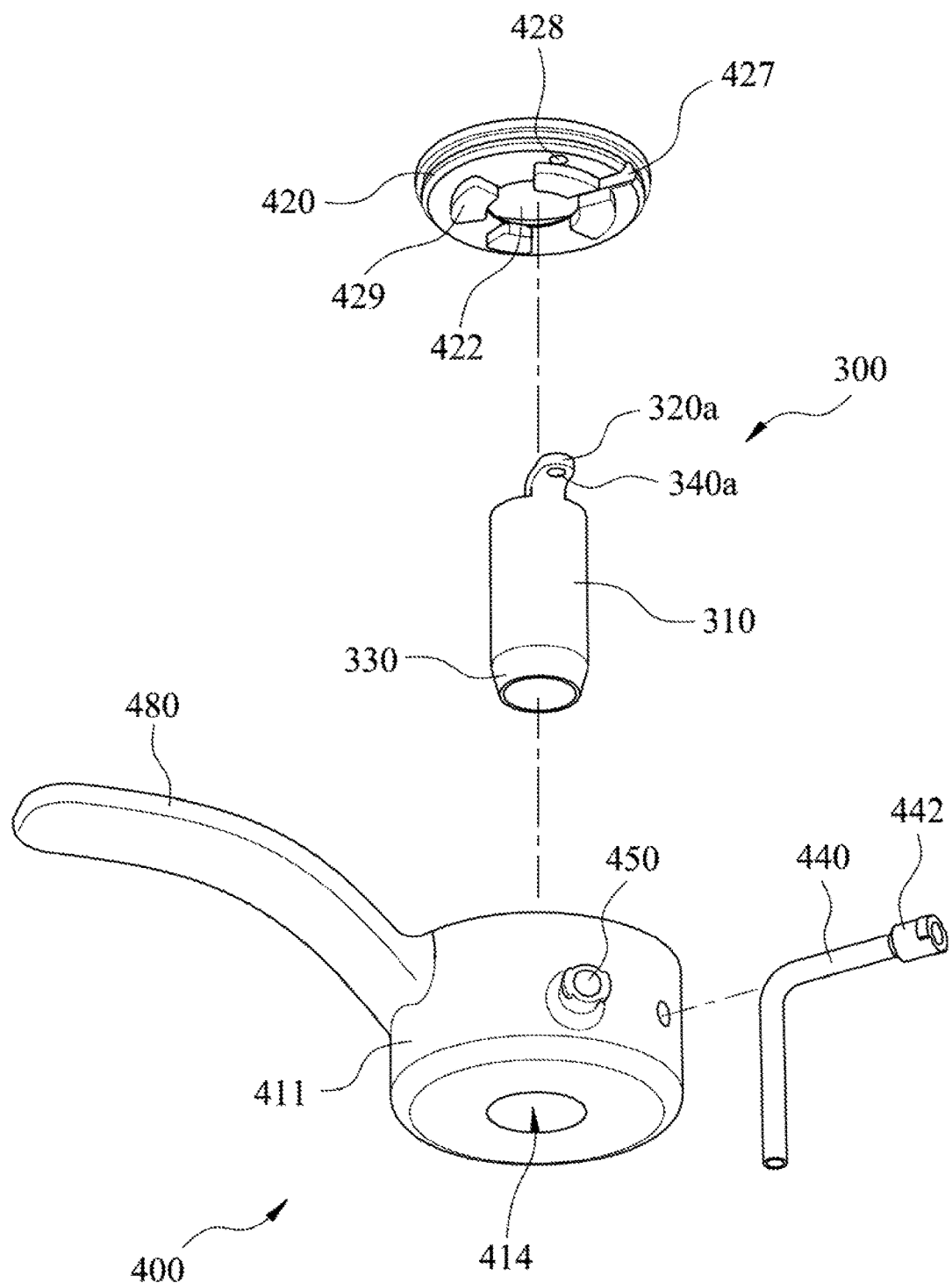
FIG. 1C shows another exploded view of the assembling surgical access device of FIG. 1A.
Figure 1D:
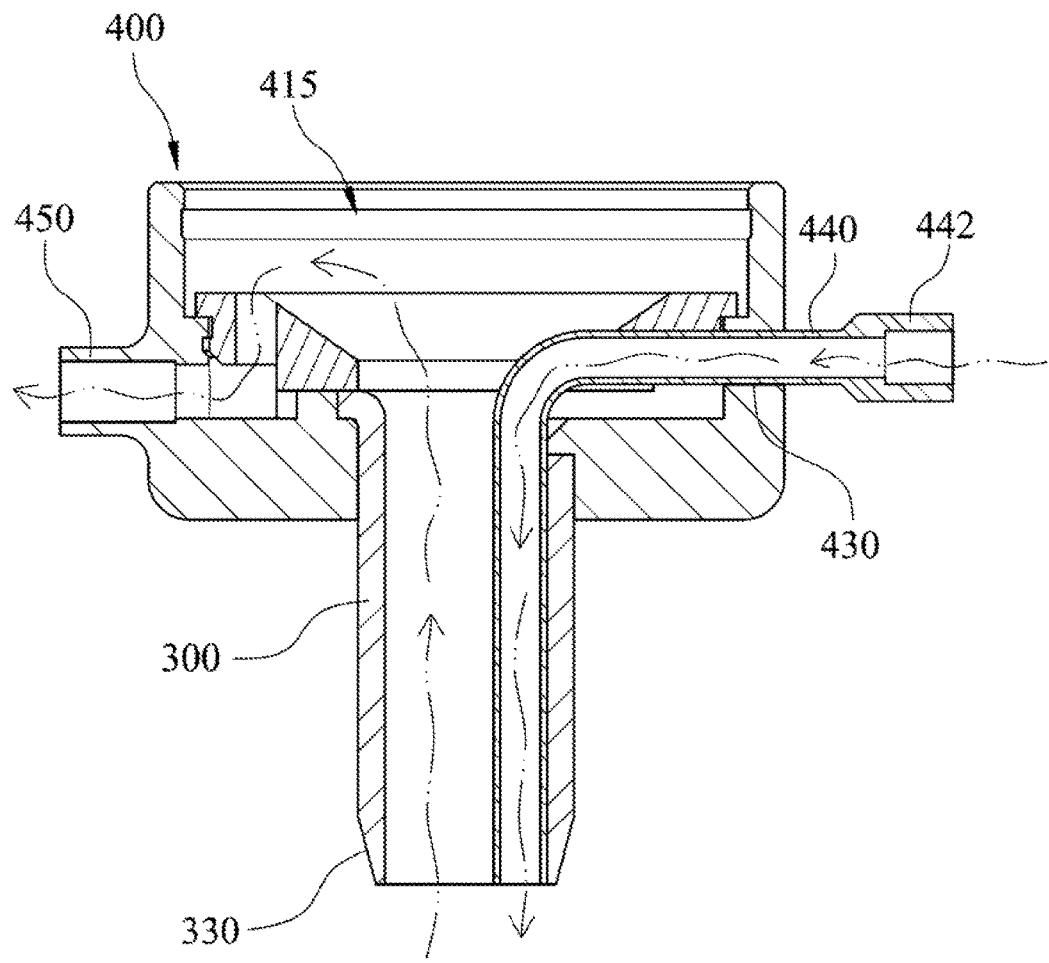
FIG. 1D shows a cross-sectional view of the assembling surgical access device of FIG. 1A.

FIG. 1A shows a schematic view of an assembling surgical access device 100 according to one embodiment of the present disclosure; FIG. 1B shows one exploded view of the assembling surgical access device 100 of FIG. 1A; and FIG. 1C shows another exploded view of the assembling surgical access device 100 of FIG. 1A; and FIG. 1D shows a cross-sectional view of the assembling surgical access device 100 of FIG. 1A. In FIG. 1B, the assembling surgical access device 100 includes a flexible tube 300 and a connecting structure 400.

The flexible tube 300 has a cylindrical shape. The flexible tube 300 includes a tube body 310, a positioning portion 320 and an inclined portion 330. The positioning portion 320 is connected to one end of the tube body 310. The inclined portion 330 is located on the other end of the tube body 320. An outer diameter of the inclined portion 330 is gradually reduced toward the other end of the tube body 310, so that the tube body 310 is easily inserted to a skin via the inclined portion 330. The positioning portion 320 includes two lug portions 320a, 320b connected to one end of the tube body 310. The two lug portions 320a, 320b have two positioning holes 340a, 340b, respectively. The lug portions 320a and the lug portion 320b are symmetrically disposed on the tube body 310. In addition, a diameter of the tube body 310 of the flexible tube 300 can be adjusted due to the flexible material thereof, so that the operating space of the surgical instruments can be increased in the human body.

The connecting structure 400 is connected to the flexible tube 300. The connecting structure 400 includes a housing 410, a tube fixing member 420, an irrigating hole 430, an irrigating tube 440, a suction hole 450, an upper slot 460, a bottom slot 470 and a grip 480. The housing 410 includes a side wall 411, an end wall 412, a fixing portion 413, a tube hole 414 and an inlaid hole 415. The side wall 411 is connected to the end wall 412. The fixing portion 413 is connected to the positioning portion 320 of the flexible tube 300. In detail, the fixing portion 413 includes a first convex part 413a and a second convex part 413b. The first convex part 413a is passed through the positioning holes 340a, and then connected to the tube fixing member 420. The second convex part 413b is passed through the positioning holes 340b, and then connected to the tube fixing member 420. The tube body 310 is disposed through the tube hole 414. The tube hole 414 is corresponding to the inlaid hole 415, and a size of the tube hole 414 is smaller than a size of the inlaid hole 415. The tube fixing member 420 is engaged into the side wall 411 so as to position the positioning portion 320 between the end wall 412 and the tube fixing member 420. The tube fixing member 420 includes a central hole 422, a first plane 424, a second plane 426, an irrigating slot 427, a draining hole 428 and a plurality of abutting parts 429. The central hole 422 is corresponding to the tube hole 414. The first plane 424 is disposed around the central hole 422. The second plane 426 is connected to the first plane. The draining hole 428 is configured to open on a connecting position of the first plane 424 and the second plane 426. The irrigating slot 427 is configured to position the irrigating tube 440. Two of the abutting parts 429 are connected to top surfaces of the two lug portions 320a, 320b, respectively. The connecting structure 400 and the flexible tube 300 may be connected by the other ways, such as thermal fusion or adhesive bonding, and will not be limited thereto. Moreover, the irrigating gating hole 430 is opened through the side wall 411 of the housing 410. One end of the irrigating tube 440 is passed through the irrigating hole 430, and the irrigating tube 440 is disposed into the flexible tube 300 for water injection. The irrigating tube 440 may be formed into a hollow circular shape or a hollow non-circular shape. The irrigating tube 440 and the inner wall of the tube body 310 may be connected by thermal fusion or adhesive bonding. The suction hole 450 is opened through the side wall 411 of the housing 410. The liquid in the connecting structure 400 can be sucked away from surgical sites via the suction hole 450 in surgical procedures. On the other hand, the water may be injected from a connecting head 442 to the irrigating tube 440, and flows smoothly to the end of the irrigating tube 440 and an inner wall of the inclined portion 330, as shown in FIG. 1D. The upper slot 460 and the bottom slot 470 are both located on an inner side of the side wall 411 of the housing 410. The tube fixing member 420 is engaged into the bottom slot 470. The grip 480 is connected to the side wall 411 for holding in surgical procedures.

Figure 2:
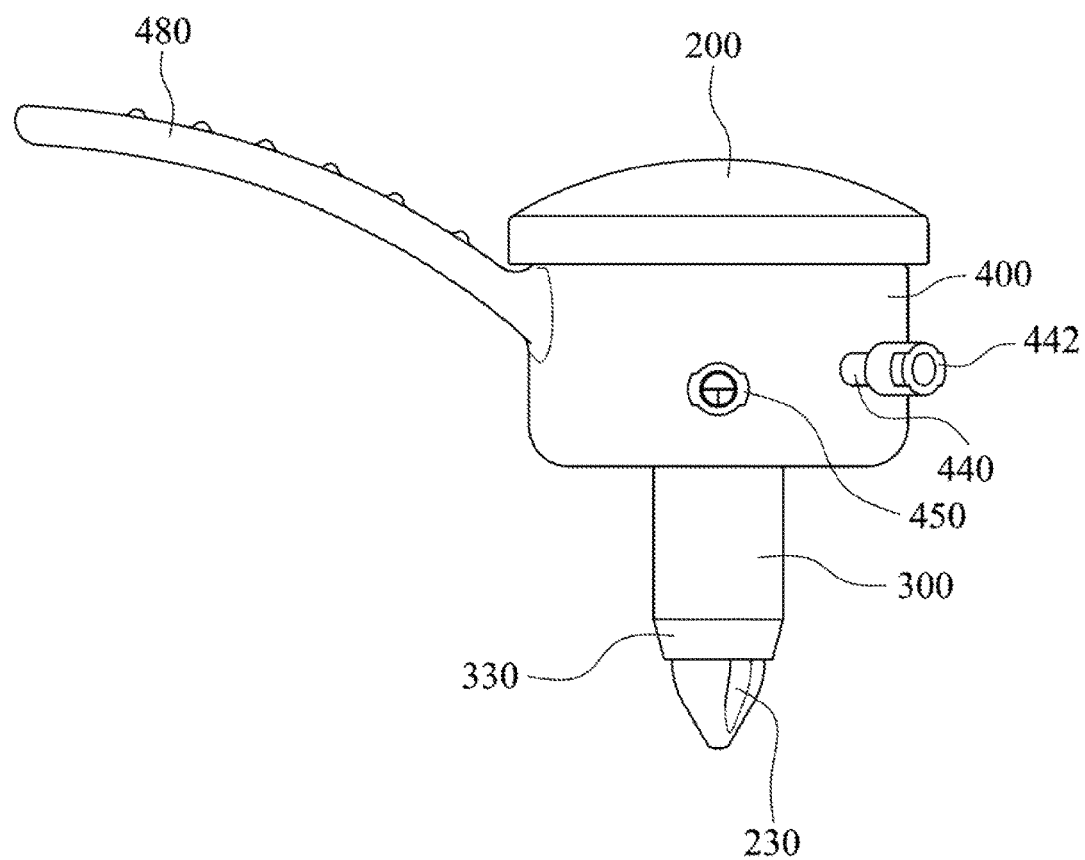
FIG. 2 shows a schematic view of an assembling surgical access device according to another embodiment of the present disclosure.
Figure 3:
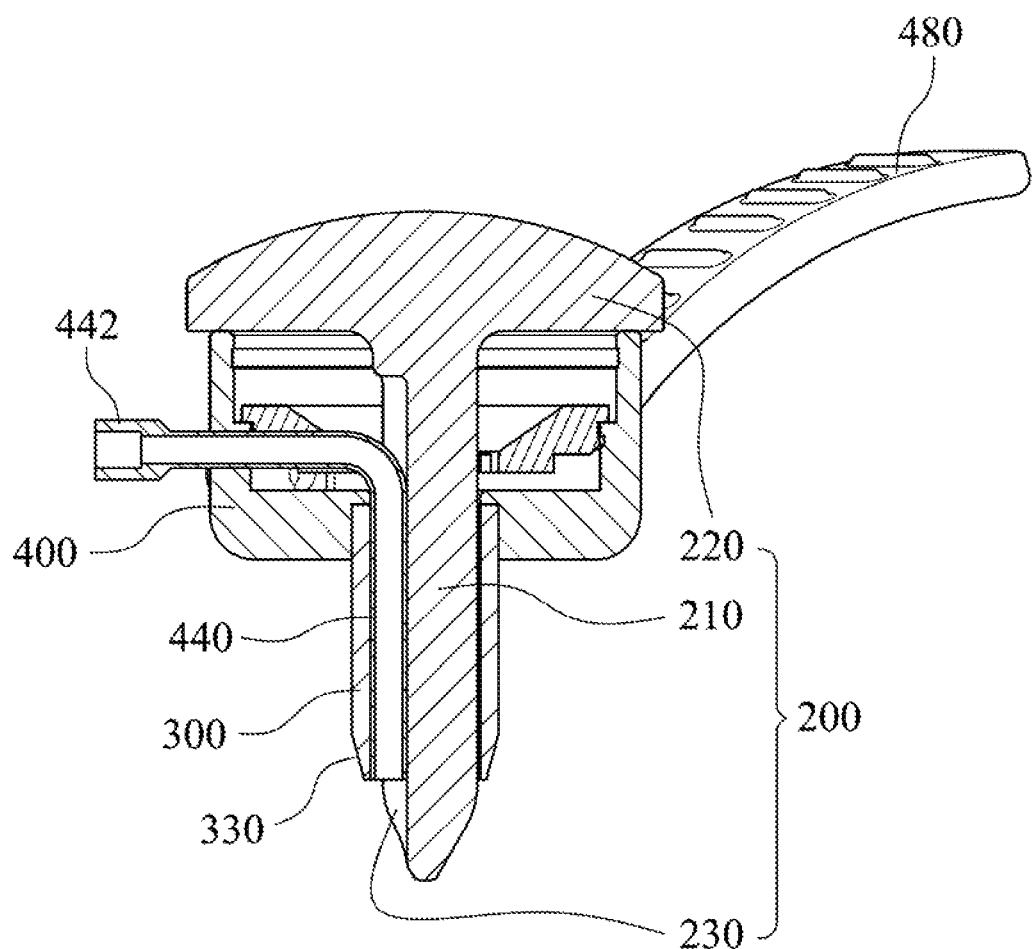
FIG. 3 shows a cross-sectional view of the assembling surgical access device of FIG. 2.

FIG. 2 shows a schematic view of an assembling surgical access device 100a according to another embodiment of the present disclosure; and FIG. 3 shows a cross-sectional view of the assembling surgical access device 100a of FIG. 2. In FIGS. 2 and 3, the assembling surgical access device 100a includes a hard sliding element 200, a flexible tube 300 and a connecting structure 400.

In FIGS. 2 and 3, the detail of the flexible to be 300 and the connecting structure 400 is the same as the embodiments of FIG. 1B, and will not be described again herein. In FIGS. 2 and 3, the assembling surgical access device 100a further includes the hard sliding element 200. The hard sliding element 200 is detachably connected to the flexible tube 300 and the connecting structure 400. The hard sliding element 200 includes a shaft 210, a top portion 220 and a recess 230. One end of the shaft 210 has a conical shape. The top portion 220 is integrally connected to the other end of the shaft 210. The recess 230 is configured from the end of the shaft 210 to the other end of shaft 210. A cross-sectional area of the top portion 220 is greater than a cross-sectional area of the shaft 210. The shaft 210 has a cylindrical shape. The top portion 220 has a circular shape. The recess 230 has an elongated shape. The shape of the hard sliding element 200 is corresponding to the shape of the flexible tube 300. In detail, a shape of the recess 230 is corresponding to a shape of an outer side of an, irrigating tube 440 of the connecting portion 400. When the hard sliding element 200 is connected to the flexible tube 300, the irrigating tube 440 can be configured to the recess 230, so that the irrigating tube 440 can be connected to the inner wall of the inclined portion 330 of the flexible tube 300. Furthermore, the end of the irrigating tube 440 is positioned at the interior of the inclined portion 330 without protruding the inclined portion 330 so as to prevent the irrigating tube 440 from interfering with a working space of the surgical sites. The water is injected from the connecting head 442 to the irrigating tube 440, and flows smoothly to the end of the shaft 210 from the irrigating tube 440. Due to the nail-shaped of the hard sliding element 200, the hard sliding element 200 connected to the flexible tube 300 and the connecting structure 400 can be used to easily penetrate and smoothly pass through the skin or achieve a rotational operation.

Figure 4:
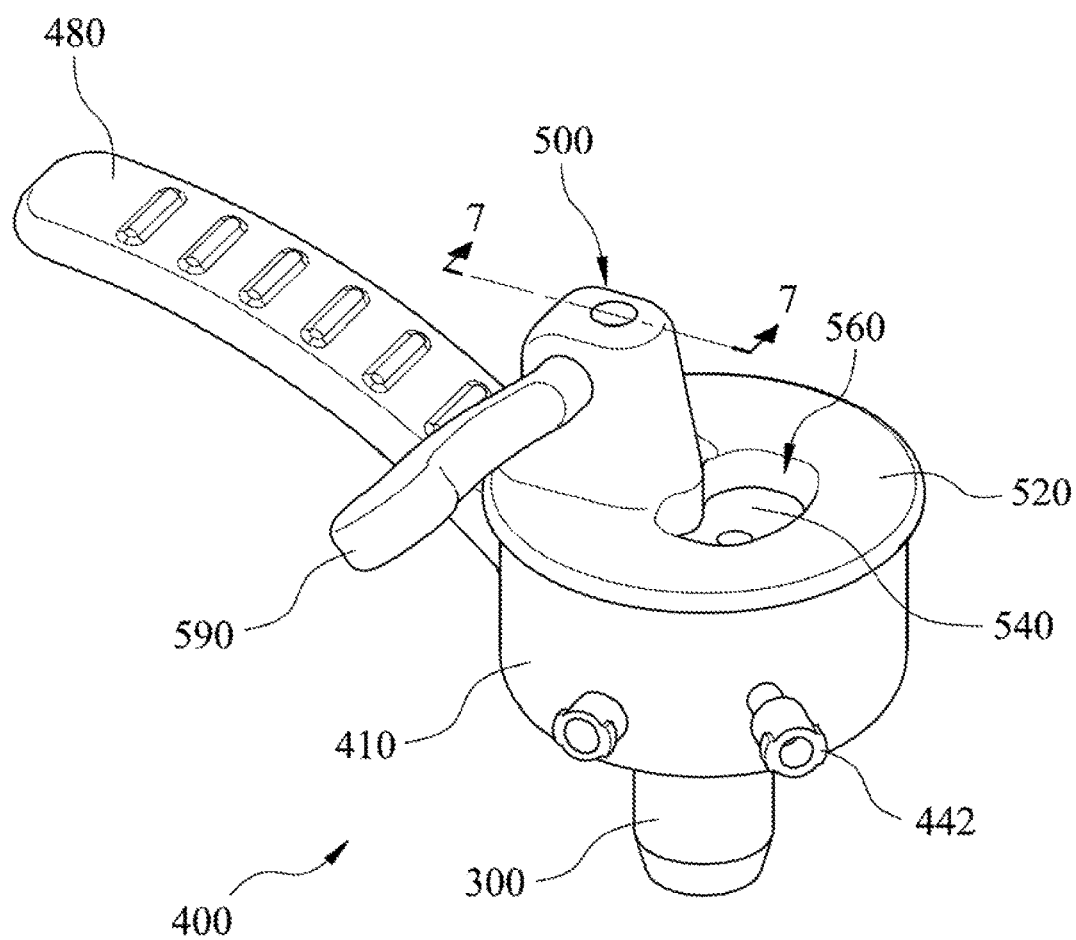
FIG. 4 shows a schematic view of an assembling surgical access device according to further another embodiment of the present disclosure.
Figure 5:
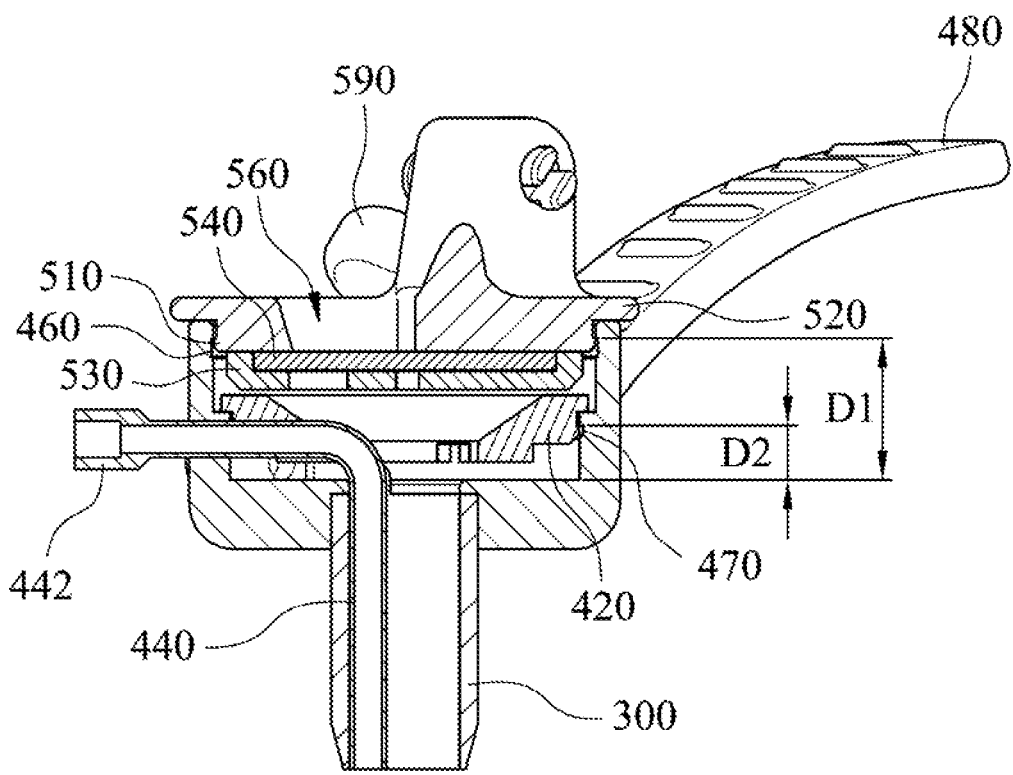
FIG. 5 shows a cross-sectional view of the assembling surgical access device of FIG. 4.
Figure 6:
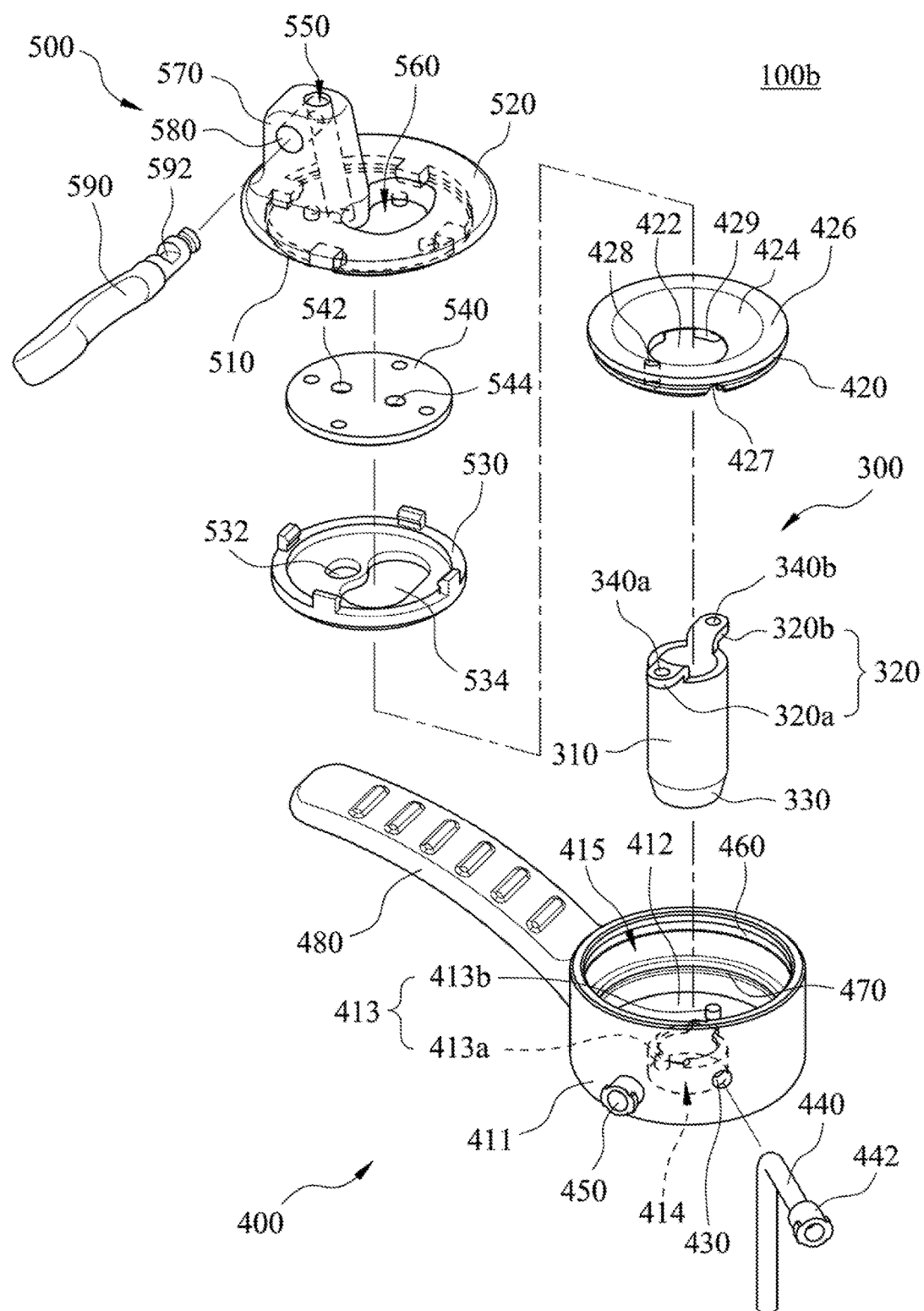
FIG. 6 shows an exploded view of the assembling surgical access device of FIG. 4.
Figure 7:
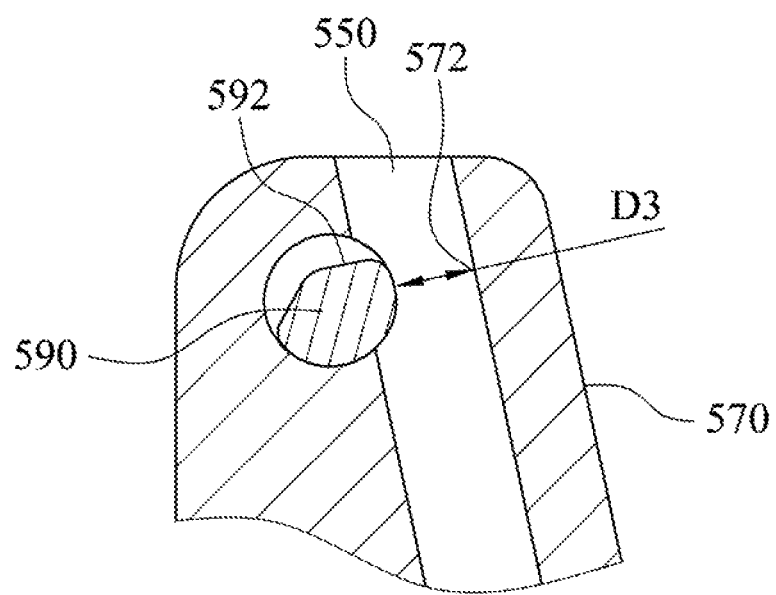
FIG. 7 shows a cross-sectional view of a part of a cover of the assembling surgical access device of FIG. 4.

FIG. 4 shows a schematic view of an assembling surgical access device 100b according to further another embodiment of the present disclosure; FIG. 5 shows a cross-sectional view of the assembling surgical access device 100b of FIG. 4; FIG. 6 shows an exploded view of the assembling surgical access device 100b of FIG. 4; and FIG. 7 shows a cross-sectional view of a part of a cover 500 of the assembling surgical access device 100b of FIG. 4. In FIG. 6, the assembling surgical access device 100b includes a flexible tube 300, a connecting structure 400 and a cover 500.

In FIGS. 4-7, the detail of the flexible tube 300 and the connecting structure 400 is the same as the embodiments of FIG. 1B, and will not be described again herein. In FIGS. 4-7, the assembling surgical access device 100b further includes the cover 500. The cover 500 includes a nose portion 510, a lid portion 520, a gasket fixing member 530, a gasket 540, a first guiding hole 550, a second guiding hole 560, a locking seat 570, a locking hole 580 and a locking switch 590. The nose portion 510 is connected to the lid portion 520, and the nose portion 510 is engaged by the upper slot 460 of the connecting structure 400, so that the cover 500 may be detachably connected to the connecting portion 400. The nose portion 510 and the lid portion 520 both have circular shapes. A cross-sectional area of the nose portion 510 is greater than or equal to a diameter of the inlaid hole 415, so that the nose portion 510 may be tightly engaged by the upper slot 460. The gasket fixing member 530 is engaged by the nose portion 510 so as to tightly dispose the gasket 540 between the nose portion 510 and the gasket fixing member 530. The gasket 540 is a transparent film and has two openings (a first gasket hole 542 and a second gasket hole 544) which are corresponding to the first guiding hole 550 and the second guiding hole 560, respectively. Moreover, the first guiding hole 550 is penetrated through the nose portion 510 and the lid portion 520. The second guiding hole 560 is also penetrated through the nose portion 510 and the lid portion 520. The first guiding hole 550 and the second guiding hole 580 are both corresponding to the tube hole 414 and the central hole 422 of the tube fixing member 420. The first guiding hole 550 is disconnected to the second guiding hole 560. The first guiding hole 550 is smaller than the second guiding hole 560. The gasket fixing member 530 includes a first fixing hole 532 and a second fixing hole 534. The first gasket hole 542 is corresponding to the first fixing hole 532 and the first guiding hole 550. The second gasket hole 544 is corresponding to the second fixing hole 534 and the second guiding hole 560. The locking seat 570 is disposed on the lid portion 520. The first guiding hole 550 is penetrated through the locking seat 570. The locking hole 580 is disposed on the locking seat 570 and communicated to the first guiding hole 550. The locking switch 590 has a curved portion 592 disposed in the locking hole 580. The locking switch 590 is rotatably connected to the locking seat 570 for varying a distance D3 between the curved portion 592 and an inner opposite position 572 of the locking seat 570 in the guiding hole 550 for stably positioning a medical device. In addition, the upper slot 460 and the end wall 412 are separated by a first distance D1, and the bottom slot 470 and the end wall 412 are separated by a second distance D2. The second distance D2 is smaller than the first distance D1.

Figure 8A:
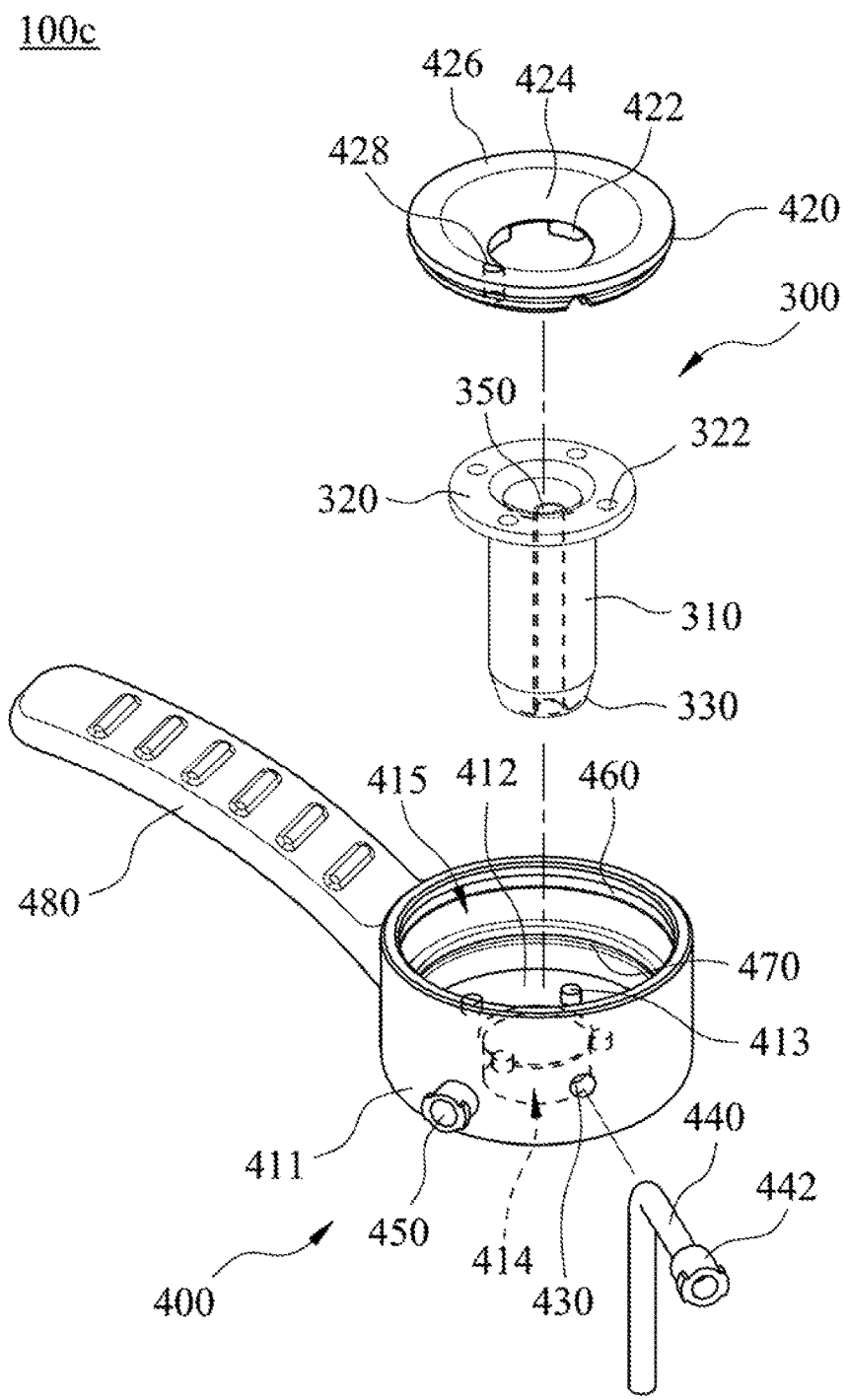
FIG. 8A shows an exploded view of an assembling surgical access device according to still further another embodiment of the present disclosure.
Figure 8B:
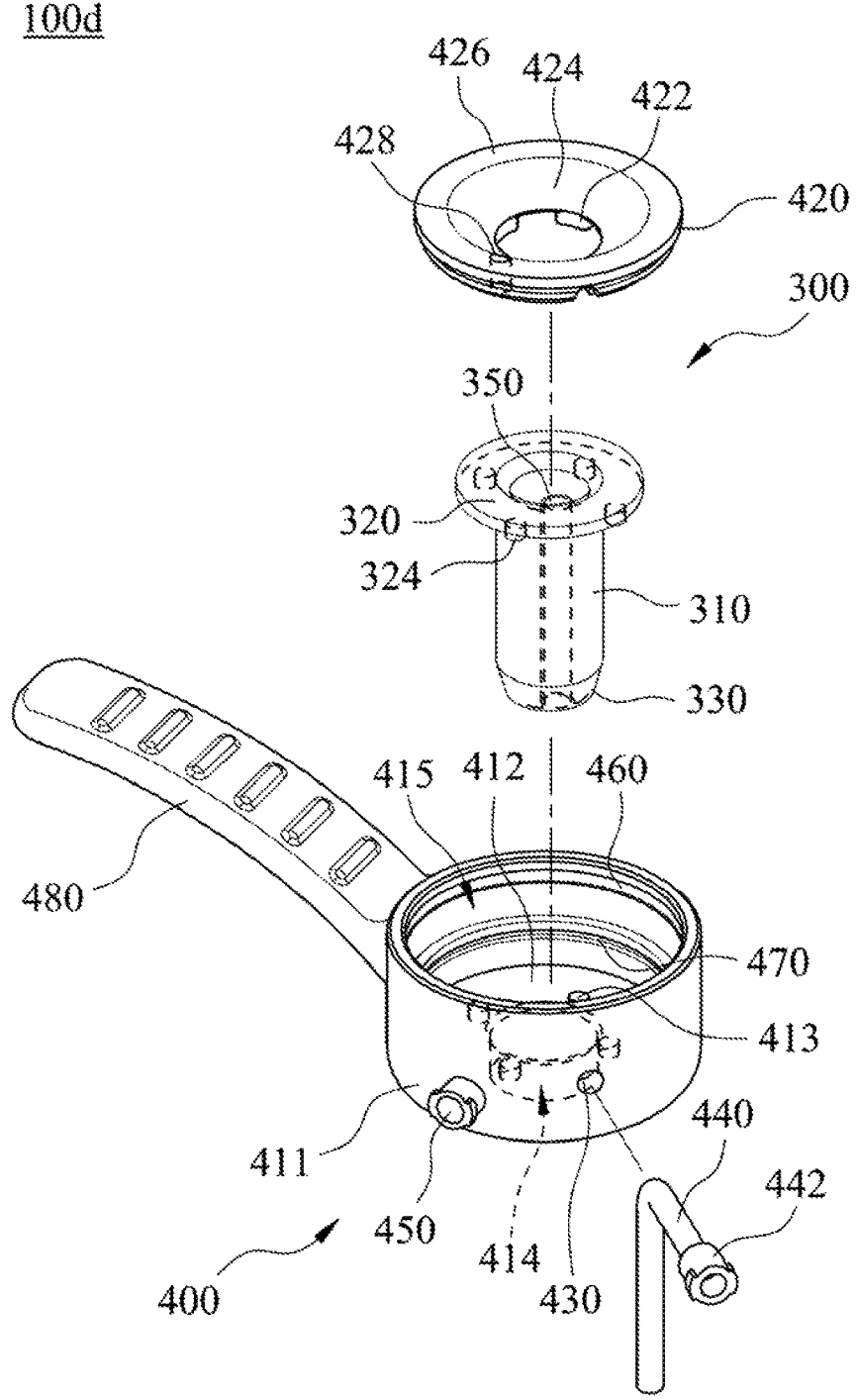
FIG. 8B shows an exploded view of an assembling surgical access device according to another embodiment of the present disclosure.

FIG. 8A shows an exploded view of an assembling surgical access device 100c according to still further another embodiment of the present disclosure. FIG. 8B shows an exploded view of an assembling surgical access device 100d according to another embodiment of the present disclosure. In FIG. 8A, the assembling surgical access device 100c includes a flexible tube 300 and a connecting structure 400.

The flexible tube 300 includes a tube body 310, a positioning portion 320, an inclined portion 330 and a fixing tube 350. The inclined portion 330 is located on the other end of the tube body 320. The positioning portion 320 having a ring shape is connected to one end of the tube body 310, and the positioning portion 320 has four positioning holes 322. The fixing to be 350 is connected to the inner wall of the tube body 310 for positioning the irrigating tube 440. The connecting structure 400 includes a housing which includes an end wall 412 and a fixing portion 413 disposed on the end wall 412. The fixing portion 413 includes four convex parts, and the four convex parts are passed through the four positioning holes 322, respectively. This structure can be used to position the flexible tube 300 and the connecting structure 400, and prevent the flexible tube 300 from rotating corresponding to the connecting structure 400. In FIG. 8B, the positioning portion 320 has a plurality of convex parts 324, the fixing portion 413 has a plurality of holes, and the convex parts are passed through the holes, respectively. This structure also can be used to position the flexible tube 300 and the connecting structure 400, and prevent the flexible tube 300 from rotating corresponding to the connecting structure 400.

Figure 9:
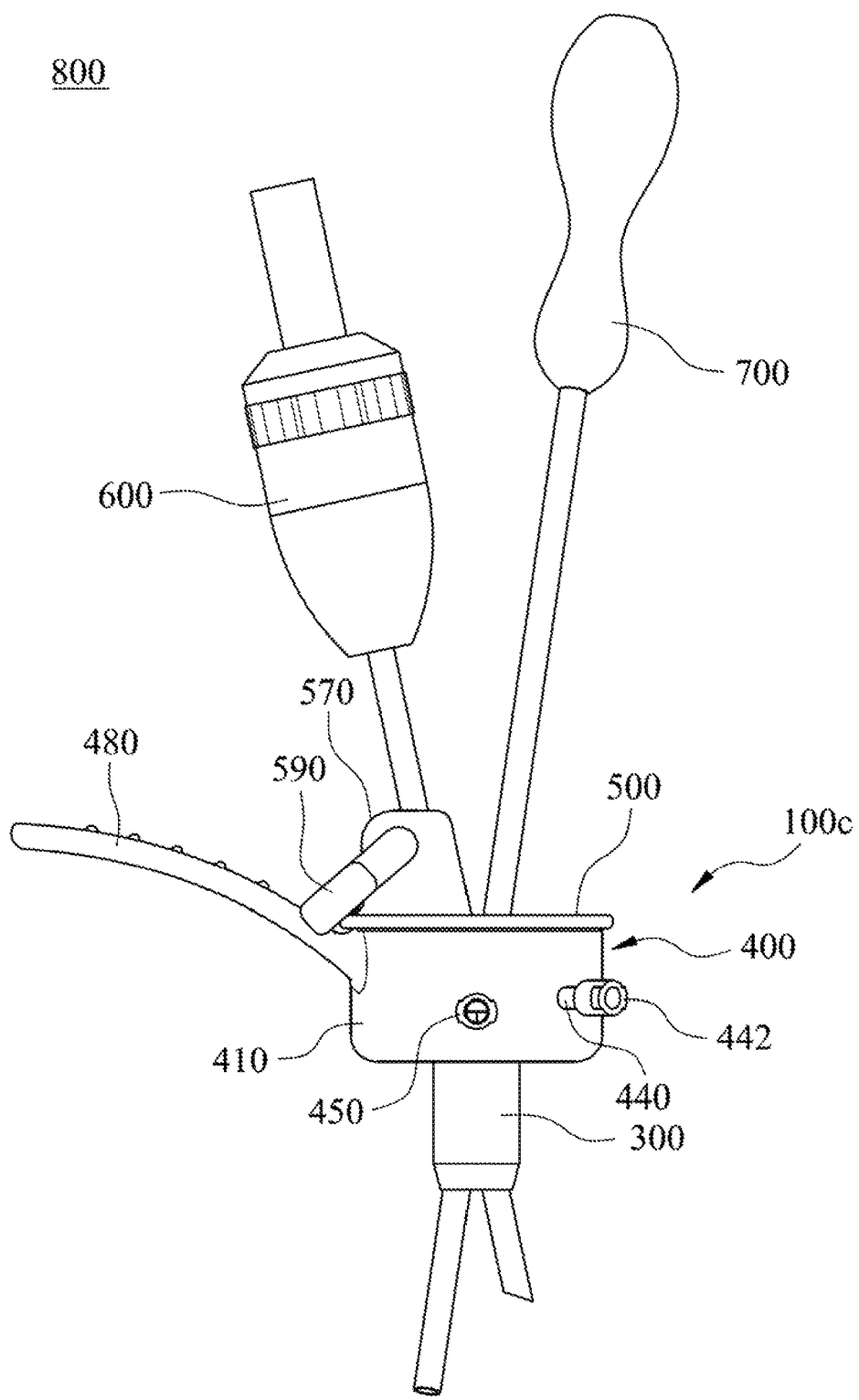
FIG. 9 shows a schematic view of an assembling surgical access device according to one embodiment of the present disclosure.
Figure 10:
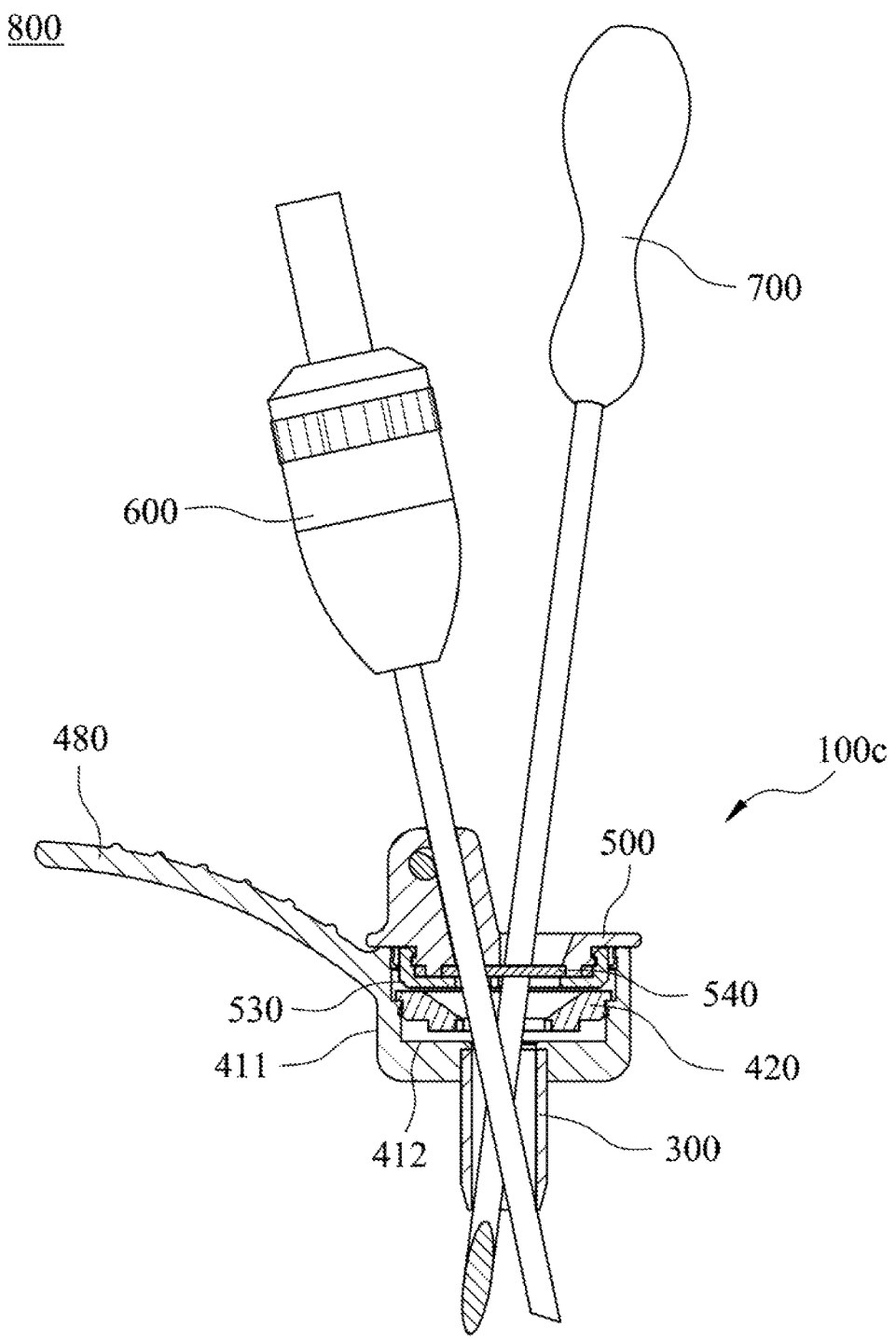
FIG. 10 shows a cross-sectional view of the assembling surgical access device of FIG. 9.

FIG. 9 shows a schematic view of an assembling surgical access device 800 according to one embodiment of the present disclosure; and FIG. 10 shows a cross-sectional view of the assembling surgical access device 800 of FIG. 9. In FIG. 9, the assembling surgical access device 800 includes an assembling surgical access device 100c, a cover 500, the endoscope 600 and a surgical instrument 700. The assembling surgical access device 100c includes a flexible tube 300 and a connecting structure 400, as shown in FIG. 8. The flexible tube 300 includes a tube body 310 and a positioning portion 320 connected to the tube body 310. The connecting structure 400 is connected to the flexible tube 300 and includes a housing 410 and a tube fixing member 420. The housing 410 includes a side wall 411, an end wall 412, a fixing portion 413, a tube hole 414 and an inlaid hole 415. The fixing portion 413 is connected to the positioning portion 320 of the flexible tube 300. The tube body 310 is disposed through the tube hole 414. The tube hole 414 is corresponding to the inlaid hole 415. The tube fixing member 420 is engaged into the side wall 411 so as to position the positioning portion 320 between the end wall 412 and the tube fixing member 420. The cover 500 includes a nose portion 510, a lid portion 520, a first guiding hole 550 and a second guiding hole 560, as shown in FIG. 6. The first guiding hole 550 is penetrated through the nose portion 510 and the lid portion 520. The second guiding hole 560 is penetrated through the nose portion 510 and the lid portion 520. The nose portion 510 is connected to the lid portion 520. The nose portion 510 is engaged by an upper slot 460 of the housing 410, and the lid portion 520 is connected to a top end of the side wall 411. The first guiding hole 550 and the second guiding hole 560 are both corresponding to the tube hole 414, the inlaid hole 415 and a central hole 422 of the tube fixing member 420. The cover 500 is detachably connected to the connecting structure 400. The endoscope 600 is passed through the first guiding hole 550, the first gasket hole 542, the first fixing hole 532, the central hole 422, the inlaid hole 415 and the tube hole 414. The surgical instrument 700 is passed through the second guiding hole 560, the second gasket hole 544, the second fixing hole 534, the central hole 422, the inlaid hole 415 and the tube hole 414. Moreover, a diameter of the first gasket hole 542 of the gasket 540 is equal to or larger than a diameter of the endoscope 600, and a diameter of the second gasket hole 544 of the gasket 540 is equal to or larger than a diameter of the surgical instrument 700. The locking switch 590 is used to position the endoscope 600. When the locking switch 590 is moved to a release position, the endoscope 600 may be freely operated by the user. On the other hand, if the locking switch 590 is moved to a clamping position, the endoscope 600 is positioned on the cover 500. The endoscope 600 may be a soft endoscope or a rigid endoscope.

Figure 11:
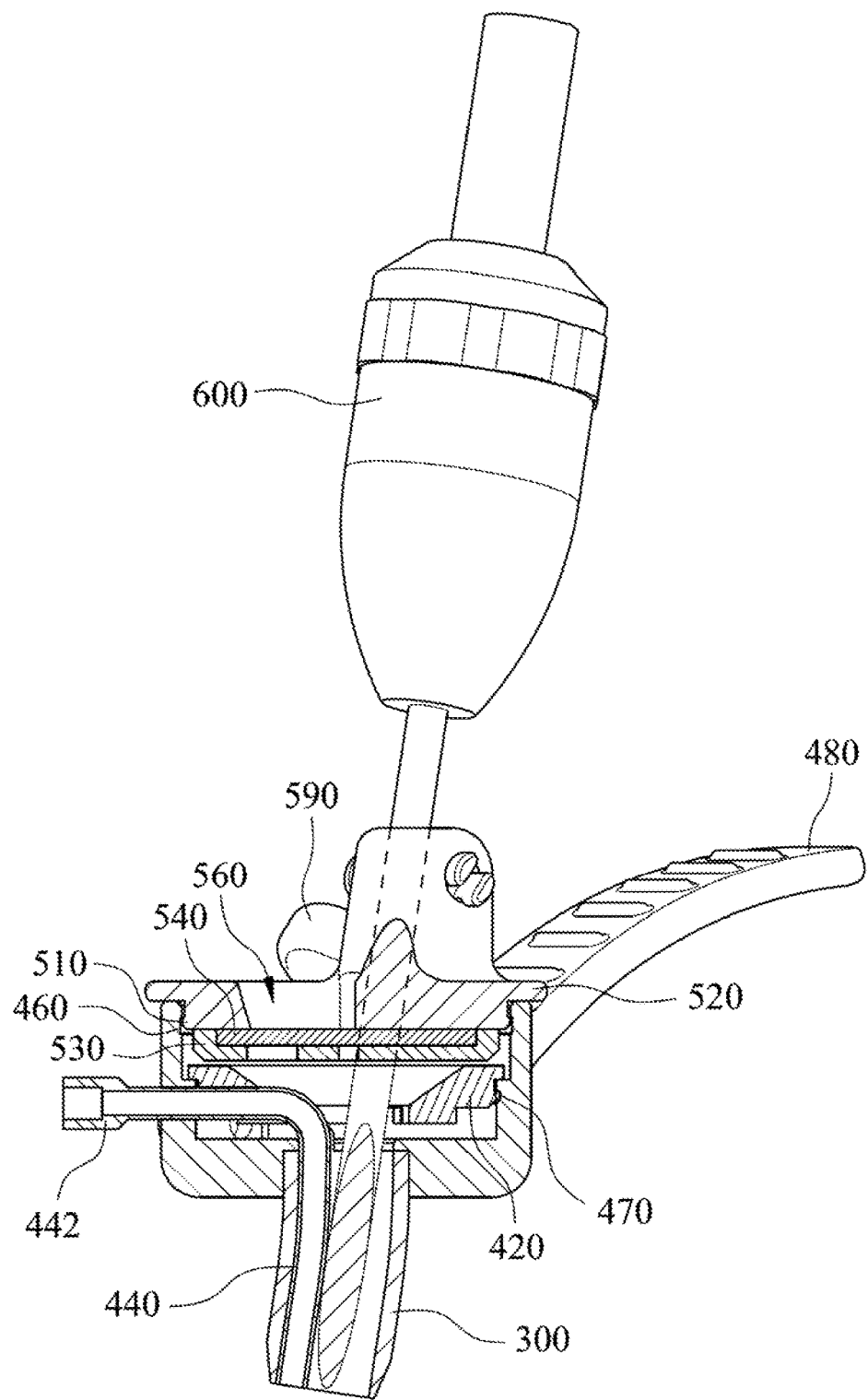
FIG. 11 shows a cross-sectional view of a flexible tube curved by an endoscope of FIG. 9.

FIG. 11 shows cross-sectional view of the flexible tube 300 curved by the endoscope 600 of FIG. 9. When the irrigating tube 440 is harder than the flexible tube 300, the irrigating tube 440 is not easily squashed by the endoscope 600 or the surgical instrument 700, so that the flexible tube 300 and the irrigating tube 440 may be curved by the endoscope 600 or the surgical instrument 700. In this case, water can be still successfully entered into the surgical site via the irrigating tube 440, and the operating space of the endoscope 600 or the surgical instrument 700 can be increased in the human body.

According to the aforementioned embodiments and examples, the advantages of the present disclosure are described as follows.

1. The assembling surgical access device of the present disclosure uses the flexible tube which can be adjusted due to the flexible material thereof, so that the operating space of the surgical instruments can be increased in the human body.

2. The assembling surgical access device of the present disclosure utilizes the hard sliding element having the nail-shaped structure, so that it can be used to easily penetrate and smoothly pass through the skin or achieve a rotational operation.

3. The assembling surgical access device of the present disclosure can employ the irrigating tube for injecting the water to the surgical sites and the suction hole for sucking away the liquid from the surgical sites in surgical procedures smoothly and conveniently.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An assembling surgical access device, comprising:
   a flexible tube comprising a tube body and a positioning portion connected to the tube body; and
   a connecting structure connected to the flexible tube, and comprising:
      a housing comprising a side wall, an end wall, a fixing portion and a tube hole, wherein the fixing portion is connected to the positioning portion of the flexible tube, and the tube body is disposed through the tube hole;
      a tube fixing member engaged into the side wall so as to position the positioning portion between the end wall and the tube fixing member;
      an irrigating hole opened through the side wall of the housing;
      an irrigating tube disposed into the flexible tube for a water injection, wherein one end of the irrigating tube is passed through the irrigating hole; and
      a suction hole opened through the side wall of the housing.

2. The assembling surgical access device of claim 1, wherein,
   the positioning portion comprises two lug portions connected to one end of the tube body, the two lug portions have two positioning holes, respectively; and
   the fixing portion comprises a first convex part and a second convex part, the first convex part is passed through one of the two positioning holes, and the second convex part is passed through the other of the two positioning holes.

3. The assembling surgical access device of claim 2, wherein,
   the flexible tube further comprises an inclined portion located on the other end of the tube body, and an outer diameter of the inclined portion is gradually reduced toward the other end of the tube body.

4. The assembling surgical access device of claim 1, wherein,
   the positioning portion comprises two lug portions connected to one end of the tube body, the two lug portions have two convex parts, respectively; and
   the fixing portion comprises a first positioning hole and a second positioning hole, one of the two convex parts is passed through the first positioning hole, and the other of the two convex parts is passed through the second positioning hole.

5. The assembling surgical access device of claim 1, further comprising:
   a hard sliding element detachably connected to the flexible tube and the connecting structure, and comprising:
      a shaft, one end of the shaft being a conical shape;
      a top portion integrally connected to the other end of the shaft; and
      a recess configured from the end of the shaft to the other end of shaft, wherein a shape of the recess is corresponding to a shape of an outer side of the irrigating tube.

6. The assembling surgical access device of claim 1, wherein the irrigating tube is formed into a hollow cylindrical shape or a hollow non-cylindrical shape.

7. The assembling surgical access device of claim 1, wherein the irrigating tube is harder than the flexible tube.

8. The assembling surgical access device of claim 1, wherein the connecting structure further comprises an upper slot and a bottom slot, the upper slot and the bottom slot are both located on an inner side of the side wall of the housing, the upper slot and the end wall are separated by a first distance, the bottom slot and the end wall are separated by a second distance, the second distance is smaller than the first distance, and the tube fixing member is engaged into the bottom slot.

9. The assembling surgical access device of claim 1, wherein the tube fixing member comprises:
   a central hole corresponding to the tube hole;
   a first plane disposed around the central hole;
   a second plane intersecting to the first plane; and
   a draining hole configured to open on an intersecting position of the first plane and the second plane.

10. The assembling surgical access device of claim 1, wherein,
    the positioning portion has a ring shape and is connected to one end of the tube body, and the positioning portion has a plurality of positioning holes; and
    the fixing portion comprises a plurality of convex parts, and the convex parts are passed through the positioning holes, respectively.

11. The assembling surgical access device of claim 1, wherein,
    the positioning portion has a ring shape and is connected to one end of the tube body, and the positioning portion has a plurality of convex parts; and
    the fixing portion comprises a plurality of positioning holes, and the convex parts are passed through the positioning holes, respectively.

12. An assembling surgical access device, comprising:
    a flexible tube comprising a tube body and a positioning portion connected to the tube body;
    a connecting structure connected to the flexible tube, and comprising:
       a housing comprising a side wall, an end wall, a fixing portion, a tube hole, an inlaid hole and an upper slot, wherein the fixing portion is connected to the positioning portion of the flexible tube, the tube body is disposed through the tube hole, and the tube hole is corresponding to the inlaid hole;

a tube fixing member engaged into the side wall so as to position the positioning portion between the end wall and the tube fixing member;

an irrigating hole opened through the side wall of the housing;

an irrigating tube disposed into the flexible tube for a water injection, wherein one end of the irrigating tube is passed through the irrigating hole; and a suction hole opened through the side wall of the housing; and a cover having a nose portion and a lid portion, wherein the nose portion is connected to the lid portion, and the nose portion is engaged by the upper slot.

13. The assembling surgical access device of claim 12, wherein the cover further comprises at least one guiding hole, the guiding hole is penetrated through the nose portion and the lid portion, and the guiding hole is corresponding to the tube hole and a central hole of the tube fixing member.

14. The assembling surgical access device of claim 12, wherein the cover further comprises:

a locking seat disposed on the lid portion;

a guiding hole penetrated through the locking seat;

a locking hole disposed on the locking seat and communicated to the guiding hole; and a locking switch having a curved portion and rotatably connected to the locking hole for varying a distance between the curved portion and an inner opposite position of the locking seat in the guiding hole.

15. The assembling surgical access device of claim 12, wherein the cover further comprises a gasket fixing member and a gasket, the gasket fixing member is engaged by the nose portion so as to tightly dispose the gasket between the nose portion and the gasket fixing member.

16. The assembling surgical access device of claim 15, wherein, the gasket fixing member comprises a first fixing hole and a second fixing hole; and the gasket comprises a first gasket hole and a second gasket hole, the first gasket hole is corresponding to the first fixing hole and a first guiding hole of the cover, the second gasket hole is corresponding to the second fixing hole and a second guiding hole of the cover, and the first guiding hole is smaller than the second guiding hole.

17. The assembling surgical access device of claim 12, wherein the irrigating tube is harder than the flexible tube.

* * * * *